(12) United States Patent
Deighan et al.

(10) Patent No.: US 9,241,655 B2
(45) Date of Patent: Jan. 26, 2016

(54) MEASURING DEVICE FOR MEASURING A PHYSIOLOGICAL PARAMETER OF AN ASPIRATE

(75) Inventors: Ciara Deighan, Birr (IE); Paul J. Daly, Tullamore (IE); Alan Fitzgerald, Edgeworthstown (IE)

(73) Assignee: Covidien LP, Mansfield, MA (US)

( * ) Notice: Subject to any disclaimer, the term of this patent is extended or adjusted under 35 U.S.C. 154(b) by 326 days.

(21) Appl. No.: 13/363,968

(22) Filed: Feb. 1, 2012

(65) Prior Publication Data

US 2012/0208285 A1 Aug. 16, 2012

(30) Foreign Application Priority Data

Feb. 1, 2011 (EP) .................................... 11000771

(51) Int. Cl.
| | |
|---|---|
| *A61M 16/00* | (2006.01) |
| *A61B 5/06* | (2006.01) |
| *A61B 5/145* | (2006.01) |
| *A61B 5/00* | (2006.01) |
| *A61M 16/04* | (2006.01) |
| *A61M 16/08* | (2006.01) |
| *A61M 1/00* | (2006.01) |
| *G01N 21/75* | (2006.01) |
| *A61J 15/00* | (2006.01) |

(52) U.S. Cl.
CPC ............. *A61B 5/061* (2013.01); *A61B 5/14539* (2013.01); *A61B 5/4238* (2013.01); *A61J 15/0084* (2015.05); *A61M 1/0025* (2014.02); *A61M 16/04* (2013.01); *A61M 16/0816* (2013.01); *A61J 1/1418* (2015.05); *A61J 15/0026* (2013.01); *A61M 16/00* (2013.01); *A61M 16/0411* (2014.02); *A61M 2205/3324* (2013.01); *A61M 2205/584* (2013.01); *G01N 21/75* (2013.01)

(58) Field of Classification Search
CPC ........ A61M 16/00; G01N 21/75; A61B 5/061
USPC ......................................... 436/163; 422/82.05
See application file for complete search history.

(56) References Cited

U.S. PATENT DOCUMENTS 5,291,879 A 3/1994 Babb et al.
5,846,836 A * 12/1998 Mallow .......................... 436/169

(Continued)

FOREIGN PATENT DOCUMENTS

EP 2168558 A1 3/2010

OTHER PUBLICATIONS

Matala Filter Media was access by the examiner on Oct. 30, 2014 from the site "http://www.matala.com.tw/biomedia/matala-filter-media.html".*
European Search Report regarding related application serial No. EP 11000771.3 dated Aug. 12, 2011, 6 pgs.

(Continued)

*Primary Examiner* — Lyle Alexander
*Assistant Examiner* — Emily Berkeley

(57) ABSTRACT

A measuring device for measuring a physiological parameter of an aspirate. The device includes a sensor element for measuring the physiological parameter, a connection port for fluid communication with a medical tube, a collection tube for aspirating and/or collecting the aspirate, a housing, wherein the sensor element is mounted within the housing and a communication passage enabling the aspirate to enter the housing from the collection tube such that the sensor element can measure the physiological parameter. Further, a method for measuring the parameter is disclosed.

2 Claims, 5 Drawing Sheets

(56) References Cited

U.S. PATENT DOCUMENTS

| | | | |
|---|---|---|---|
| 7,052,474 B2* | 5/2006 | Castell et al. | 600/593 |
| 8,210,168 B2* | 7/2012 | Swisher | 128/202.22 |
| 2003/0040671 A1 | 2/2003 | Somogyi et al. | |
| 2004/0077093 A1 | 4/2004 | Pan | |
| 2004/0158138 A1 | 8/2004 | Kilcoyne et al. | |
| 2006/0060202 A1* | 3/2006 | Flynn et al. | 128/207.14 |

OTHER PUBLICATIONS

European Communication pursuant to Article 94(3) EPC for Application No. 11 000 771.3-1660 dated Oct. 22, 1013, 3 pages, Munich, Germany.

European Summons to attend oral proceedings pursuant to Rule 115(1) EPC dated Aug. 4, 2014 in related application serial No. EP 11000771.3, 4 pages.

* cited by examiner

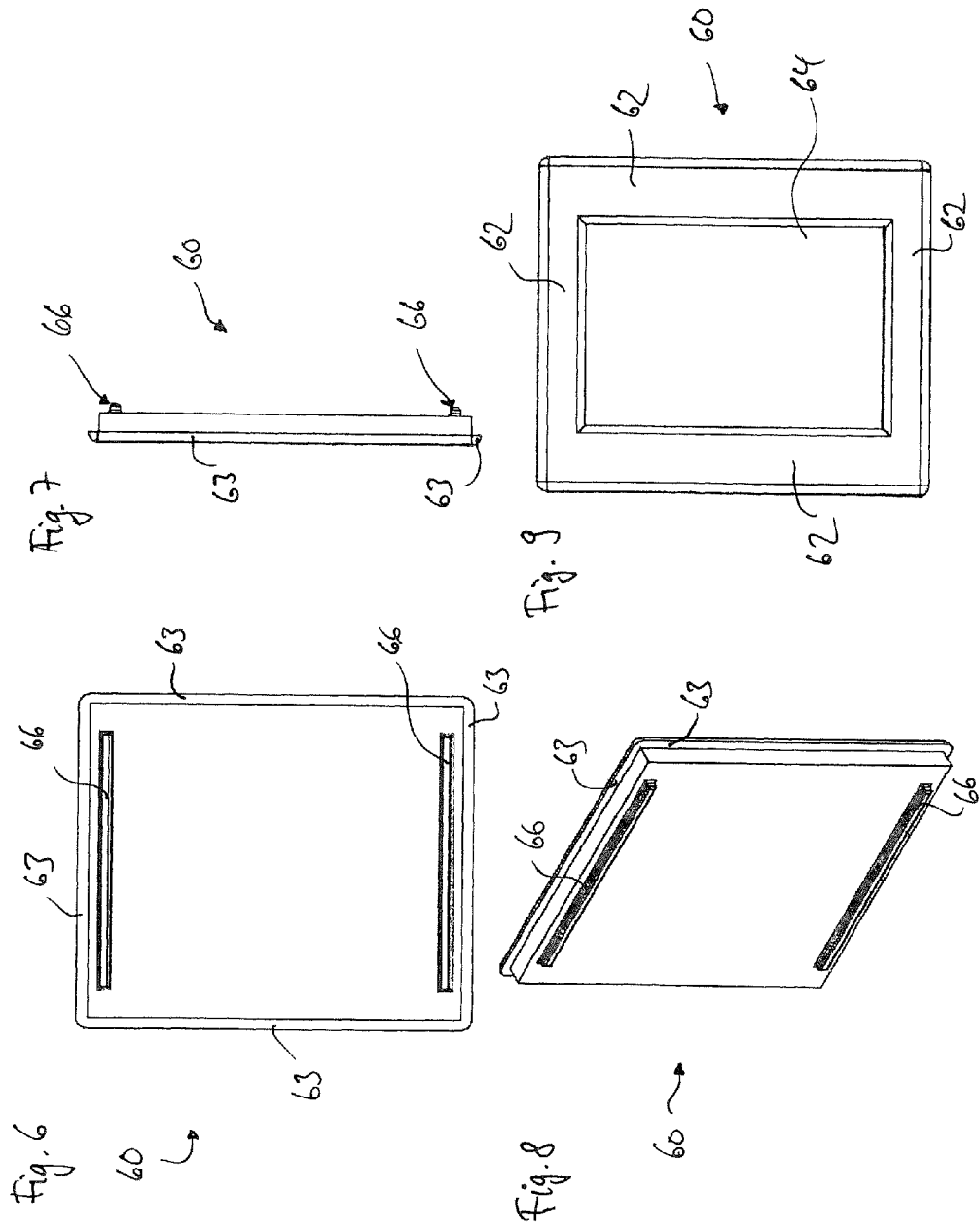

MEASURING DEVICE FOR MEASURING A PHYSIOLOGICAL PARAMETER OF AN ASPIRATE

BACKGROUND

The present disclosure relates to a measuring device for measuring a physiological parameter of an aspirate. The measuring device comprises at least one physiological parameter sensor element.

In clinical medicine there are many situations where detecting the location of a medical tube within a patient is important. For example, when positioning a feeding tube through the nose of a patient, it is essential that the end of the feeding tube passes into the patient's esophagus and not into the lung/trachea. If the end of the feeding tube is positioned in the trachea rather than in the stomach, aspiration of the feeding solution into the patient's lungs may occur. Further, when positioning a medical tube through the nose of a patient into the patient's trachea/lung, it has to be checked if the end of the medical tube really passes into the lung/trachea and not into the esophagus. In this regard, devices are known for detecting $CO_2$ values of aspirates in order to check if a medical tube is in the trachea or in the esophagus.

Improper positioning of enteral feeding tubes into the trachea resulting in respiratory distress or death has been described in the literature. In practice, tube position should be checked following initial insertion, before administering each feed, before giving medication, following vomiting, retching or coughing or if there is evidence of tube displacement, for example, if the tape is loose or the visible tube appears longer of kinked.

Currently, the location of a medical tube within the body of a patient is routinely detected by the use of imaging equipment, such as X-ray. However, such a procedure requires transportation of the patient to an X-ray facility. This is both inconvenient and costly and is particularly stressful in those instances where the medical tube has repeatedly to be repositioned, thus requiring repeated reinsertion and X-rays.

US 2004/0158138 A1 discloses an implantable monitoring probe having a sensor for detecting pH and a transmitter for transmitting data to an external receiver. The probe is implanted in the esophagus or other body lumen of a patient to aid in the detection of gastroesophageal reflux disease. US 2003/0040671 A1 discloses a medical tube for insertion into a tracheal tube of a patient wherein the medical tube includes a pH sensing element. U.S. Pat. No. 7,052,474 B2 discloses a pharyngoesophageal monitoring system that includes multiple internal references probes detecting acid reflux and monitoring pH levels.

However, these measuring devices have to be inserted into a medical tube and in the patient's body. To evaluate the measured value further equipment, e.g. transmitters and data recorders, is necessary. Such equipment is extensive and costly. The current practice by clinicians of obtaining the pH value of a patient's aspirate is to draw up aspirate fluid with a syringe and place a drop of this fluid onto a pH indicator strip. However, this procedure is critical for clinicians as regards the bacteria contained in the aspirate fluid.

SUMMARY OF THE DISCLOSURE

In one aspect, a measuring device generally comprises a sensor element for measuring the physiological parameter, a connection port for fluid communication with a medical tube, a collection tube for aspirating and/or collecting the aspirate, a housing, wherein the sensor element is mounted within the housing and a communication passage enabling the aspirate to enter the housing from the collection tube such that the sensor element can measure the physiological parameter.

In another aspect, a measuring device for measuring a physiological parameter of an aspirate generally comprises a sensor element for measuring the physiological parameter; a connection port for fluid communication with a medical tube; a collection tube for aspirating and/or collecting the aspirate; a housing, wherein the sensor element is mounted within the housing; a communication passage enabling the aspirate to enter the housing from the collection tube such that the sensor element can measure the physiological parameter; and a filter element disposed between the sensor element and the communication passage. The housing comprises a first support for supporting the sensor element, a second support for supporting the filter element and a lid having a transparent window.

In yet another aspect, a method for measuring a physiological parameter of an aspirate generally comprises connecting a connection port of the measuring device to a medical tube for fluid communication of the aspirate with a physiological parameter sensor element mounted in a housing of the measuring device; aspirating the aspirate out of the medical tube via a collection tube and a communication passage of the measuring device into the housing; and measuring of the physiological parameter by means of the sensor element.

BRIEF DESCRIPTION OF THE DRAWINGS

FIG. 6 is a back view of the lid shown in FIG. 1;

FIG. 7 is a side view of the lid of FIG. 6;

FIG. 8 is a perspective of the lid of FIG. 6; and

FIG. 9 is a front view of the lid of FIG. 6.

DETAILED DESCRIPTION OF THE DRAWINGS

Figure 1:
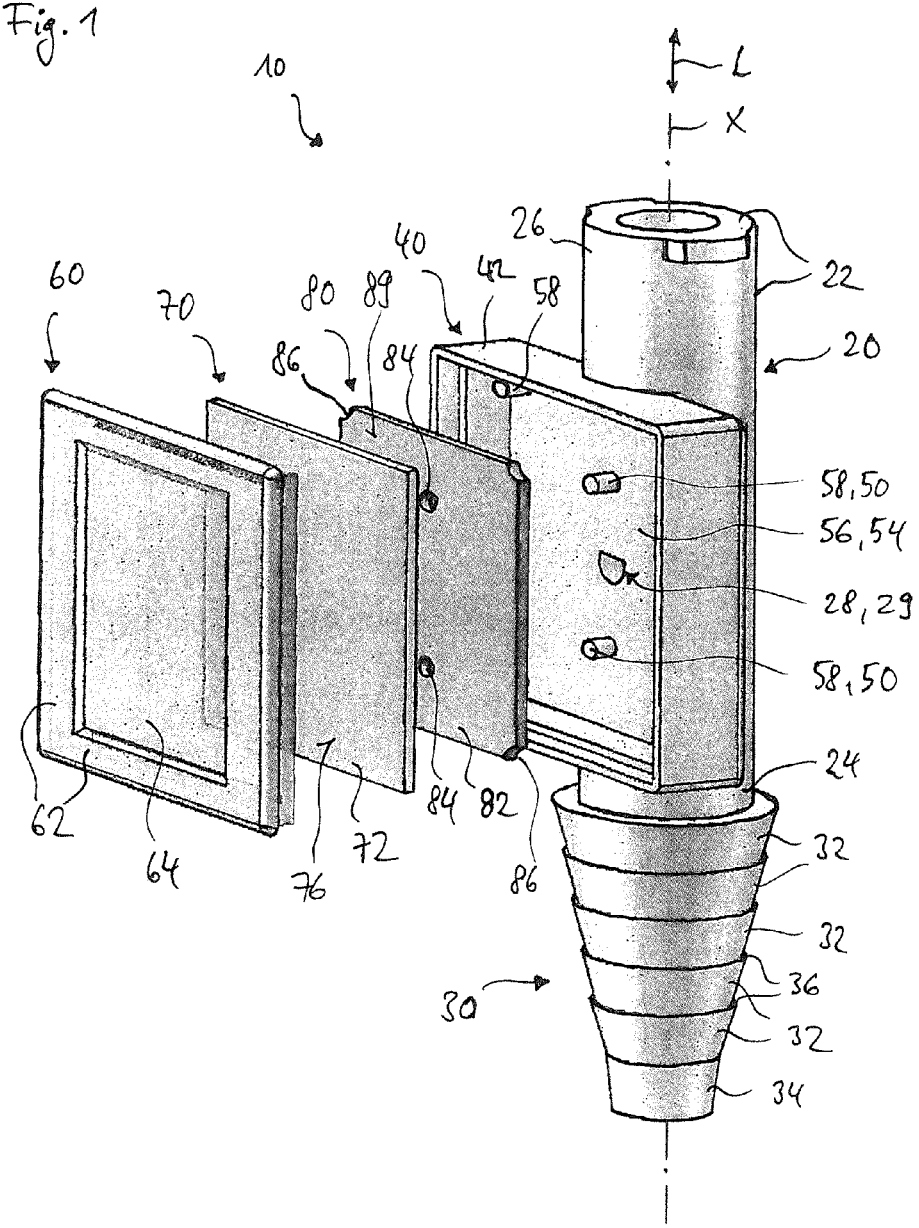
FIG. 1 is an exploded perspective of the measuring device according to one embodiment of the present invention.
Figure 2:
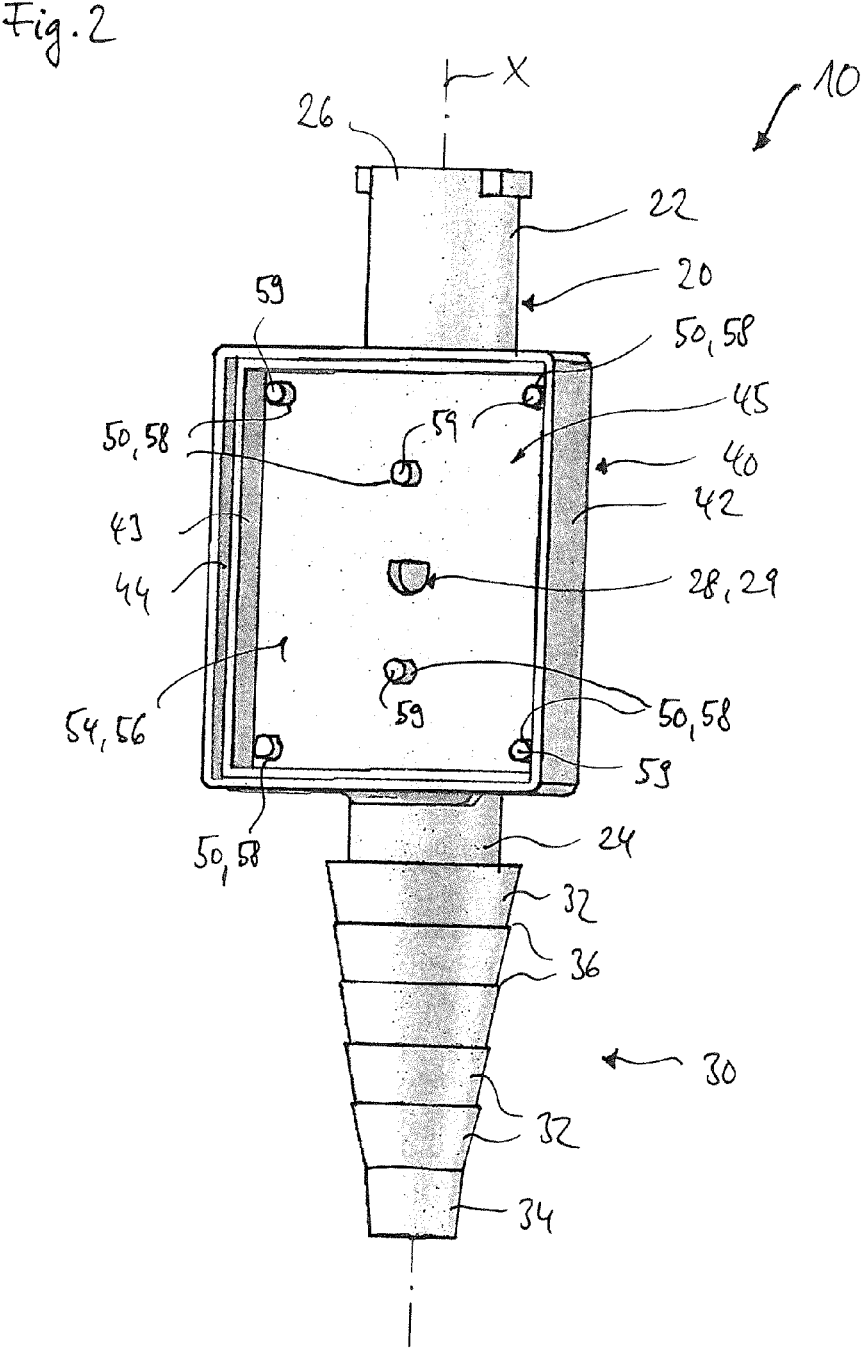
FIG. 2 is a perspective similar to FIG. 1 but only showing a part of the housing, the collection tube and the connection port.
Figure 3:
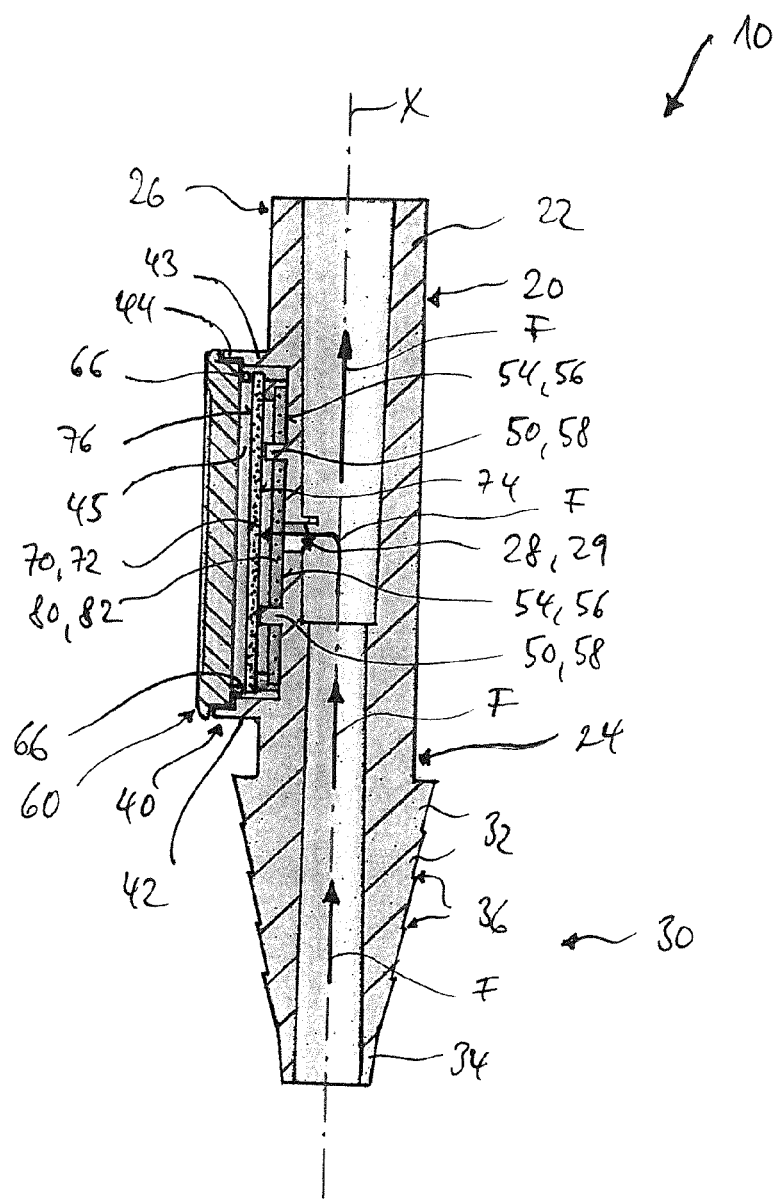
FIG. 3 is a cross-sectional view of the assembled measuring device according to FIGS. 1 and 2 along the longitudinal direction L in FIG. 1.
Figure 4:
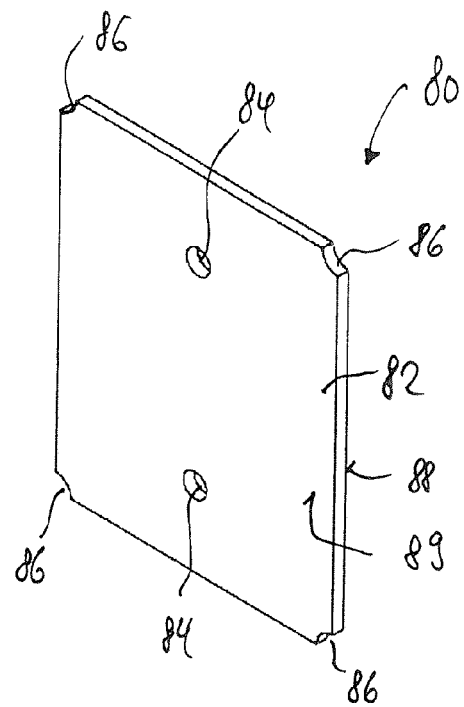
FIG. 4 is a perspective view of the filter element of the measuring device according to FIGS. 1 to 3.
Figure 5:
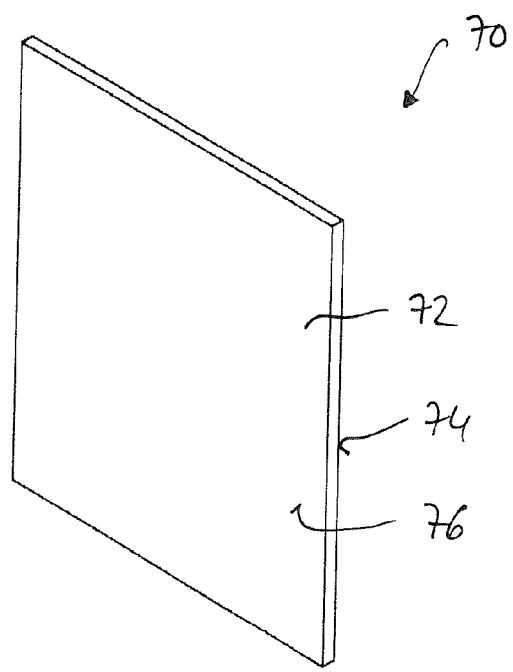
FIG. 5 is a perspective view of the sensor element of the measuring device according to FIGS. 1 to 3.

FIGS. 1 to 9 show a preferred embodiment of a measuring device 10 for measuring a physiological parameter of a fluid, such as an aspirate, drawn up from the human body by means of a medical tube (not shown). FIG. 1 shows an exploded view of a device 10 with a housing 40, a lid 60 of the housing 40, a sensor element 70 and a filter element 80. The perspective view of FIG. 2 shows the measuring device 10 according to FIG. 1 without the lid 60, the sensor element 70, and the filter element 80. FIG. 3 shows a cross-sectional view of an assembled device 10 of FIG. 1. FIG. 4 is a perspective view of the filter element 80. FIG. 5 is a perspective view of the sensor element 70. FIGS. 6 to 9 show different views of the lid 60.

The housing 40 is attached to or formed integrally with a collection tube 20 having a first end 24 and a second end 26. The collection tube 20 can be of substantially circular cross-section and has a wall 22 to provide a channel for fluid communication F (see arrows in FIG. 3) between the medical tube and the housing 40.

A connection port 30 is attached to or formed integrally with the collection tube 20 at the first end 24. The connection port 30 comprises a plurality of port sections 32 which are tapered and stepped at an outer surface such that a plurality of abutments 36 is formed. The terminal end of the connection port 30 typically has an end section 34. The outer surface of the end section 34 is typically inclined in a different angle compared to the port sections 32. This configuration of the connection port 30 provides the possibility to connect the measuring device 10 to the medical tube, for example by means of a connector (not shown), preferably a Y-shaped connector having two ports.

The connection port 30 is suitable for being inserted into such a connector port, an end portion of a medical tube, or an adapter mounted to the end portion of the medical tube. The abutments 36 enable to slip over the connector port or the medical tube and to provide a close and tight connection.

A communication passage 28 comprises a through hole or opening 29 providing fluid communication between the collection tube 20 and a receiving or hollow space 45 of the housing 40 and enabling the aspirate to enter the housing 40 such that the sensor element 70 can measure the physiological parameter. In one or more embodiments of the invention, the communication passage 28 can comprise a valve. The valve can be a spigot valve and can be formed such that the aspirate is drawn from the collection tube 20 into the housing 40. In some cases, passage 28 can be formed such that the fluid, such as the aspirate, can be drawn from collection tube 20 into the housing 40, such as into space 45. The receiving space 45 can be configured to receive the sensor element 70 and the filter element 80.

The second end 26 of the collection tube 20 can be formed such that a syringe or the like can be connected with the measuring device to provide a vacuum to draw up the aspirate.

As exemplarily illustrated, the collection tube 20 and the connection port 30 extend in a longitudinal direction L corresponding to the direction of a longitudinal axis X of the measuring device 10, as can be taken from FIGS. 1 to 3.

The housing 40 comprises a wall 42 having a first wall section 43 and a second wall section 44. The first and second wall sections 43, 44 can have different thicknesses. The first wall section 43 can be thicker than the second wall section 44 such that a shoulder can be formed to support the lid 60 in the closed condition of the housing 40. The lid 60 can be removably connected to the wall 42, for example, at the shoulder. As can be taken from FIGS. 1, 3 and 6 to 9, the lid 60 comprises a frame 62 having a projection 63, a transparent window 64 and supporting edges 66 or shims. When closing the housing 40 with the lid 60, the projection 63 contacts or engages the wall 42 and mainly is supported on above-mentioned shoulder formed by the first and second wall sections 43, 44.

To enable visual evaluation of the value measured/detected by the sensor element 70 within the receiving space 45 the transparent window 64 has a high percentage of area compared to the frame 62. In an alternative embodiment, substantially the entire lid 60 and/or wall 42 can be made of transparent material. To visually evaluate the value measured by the sensor element 70 an evaluation unit (not shown), for example a pH colour reference chart, can be attached to the frame 62 or any other part of the housing 40. As shown in FIGS. 6 to 9, the frame 62 and/or the projection 63 comprise inclined or rounded edges.

Each of the sensor element 70 and the filter element 80 comprises an absorbable sheet 72, 82 for absorbing at least part of the aspirate. The absorbable sheet 72 has an inner surface 74 and an outer surface 76. The absorbable sheet 82 has an inner surface 88 and an outer surface 89. Preferably, both sheets 72, 82 are made of paper material. In the present embodiment, the physiological parameter to be measured is the pH value of the aspirate. Therefore, the absorbable sheet 72 is pH indicative paper material. As shown in FIGS. 1 and 4, the absorbable sheet 82 of the filter element 80 has two openings 84 and four rounded corners 86 which will be discussed below in further detail in connection with the support of the filter element 80 and the sensor element 70.

As can be taken from FIGS. 1 to 3, the housing 40 comprises a first support 50 for supporting the sensor element 70 and a second support 54 for supporting the filter element 80. The first support 50 and the second support 54 are configured and positioned relative to each other such that the sensor element 70 being spaced apart from the filter element 80, as can be taken from FIG. 3. In other words, the filter element 80 is disposed between the sensor element 70 and the communication passage 28. The filter element 80 prevents flooding of the receiving space 45 when the aspirate is drawn up through the collection tube 20 and via the communication passage 28 into the receiving space 45, i.e. into the housing 40.

Generally speaking, the first support 50 and/or the second support 54 comprises at least one plate 56, pin 58, edge 66 and/or shim.

When assembling the device 10 the absorbable sheet 82 is positioned with its inner surface 88 on the plate 56 as the supporting structure for the second support 54. The plate 56 can be part of the housing 40, such as the back wall of the housing 40. To bring the absorbable sheet 82 in this end position it is put into the housing 40 such that the corresponding pins 58 extend through the openings 84 and engage the corners 86. As a next step, the absorbable sheet 72 of the sensor element 70 is assembled in the housing 40 such that the end faces 59 of the pins 58 contact the inner surface 74 of the absorbable sheet 72 to provide the first support 50 for the sensor element 70. In this position, the outer surface 89 of the absorbable sheet 82 is being spaced apart from the inner surface 74 of the absorbable sheet 72. Next the lid 60 is disposed on the wall 42 as mentioned above to close the housing 40 and to further support the sensor element 70 by means of the supporting edges 66 of the lid 60 which can be seen in particular from FIGS. 3 and 7. After attachment of the lid 60 to the wall 42, the supporting edges 66 and the pins 58 support the sensor element 70 from both sides of the sensor element 70.

In order to conduct the method for measuring the physiological parameter of the aspirate in a first step, the connection port 30 is connected directly or indirectly to a medical tube for fluid communication as mentioned above. Next, the aspirate of the human body is aspirated out of the medical tube via the collection tube 20 and a small amount of the aspirate is drawn via the communication passage 28 into the housing 40 such that the sensor element 70 can detect or measure the parameter, in particular the pH value. The direction of fluid communication can be taken from the arrows F shown in FIG. 3.

To aspirate or draw the fluid out of the medical tube a syringe or the like is attached to the collection tube 30.

As disclosed above, in one embodiment the measuring device comprises a sensor element for measuring the physiological parameter, a connection port for fluid communication with a medical tube, a collection tube for aspirating and/or collecting the aspirate, a housing, wherein the sensor element is mounted within the housing and a communication passage enabling the aspirate to enter the housing from the collection tube such that the sensor element can measure the physiological parameter.

Once position of the medical tube has been confirmed, an additional use of an embodiment of this invention can be for example that both pH and the level of gastric aspirate can be checked simultaneously by the measuring device, preferably in conjunction with an attached syringe. It is a standard practice in institutions to check aspirates in gastrically-fed patients to determine if formula is being retained in the stomach, theoretically placing the patient at risk for gastroesophageal reflux and potential aspiration. The general practice is to hold feedings for gastric residual volume of greater than 150-200 ml. Obtaining the pH of the gastric aspirate can also aid in determining if formula is being retained in the stomach, as the presence of formula will raise the pH of the aspirate, making it more alkaline.

At least one embodiment of the invention can help reduce the amount of times a patient's tube position needs to be checked radiographically. Measuring the pH of the aspirate is a useful indicator of tube position because gastric fluid is considered to have low pH (acidic-pH <6), while fluid aspirated from the pleural space or lung has a much higher pH (alkaline-pH ≥7). For example, pH strips can be used to differentiate between gastric and respiratory tube placement.

At least one embodiment of the invention can aid in determining tube placement and, once the tube is in the correct position, if formula is being retained in the stomach.

At least one embodiment of the present invention relates to the application of pH indicator paper for the sensor element in the closed system of the measuring device which connects between the enteral access or giving device and a syringe which will aspirate or collect an aspirate of the stomach contents for both visual evaluation and pH measurement. A small amount of the aspirated fluid can be drawn in using a syringe vacuum via a spigot valve to the pH paper located behind the viewing window of the lid. A piece of absorbent paper or a filter is also placed between the fluid entrance from the spigot valve and the pH paper, in order to prevent the viewing window from flooding with gastric residue or fluid, so that the colour change on the pH can be easily seen by the user. A pH colour reference chart can also be supplied with the device. Preferably, this system or device is a single use, disposable device.

As to the terms used in the present application, the measuring device can also be designated as meter assembly or aspirate meter. "Measuring" could be substituted or added by "detecting". As used herein, the collection tube serves for aspirating and/or collecting the aspirate out of the medical tube. The aspirate may also be designated as human body fluid.

As to the fluid communication between the connection port and the medical tube, the measuring device can be connected directly or indirectly to the medical tube. Preferably, the measuring device is connected via its connection port and a connector assembly to the medical tube. This connector has at least one port, preferably two ports having a Y-shape.

As used herein, the term "medical tube" means all types of tubes or devices which may be inserted into a patient's body, for example catheters and medical instruments. As used herein, "catheters" include such items as feeding tubes, catheters, pH catheters, endotracheal tubes and stomach pump tubes.

Although a pH sensor is described herein as a preferred embodiment, those skilled in the art will appreciate that any of a variety of other physiological parameters or values can be detected and measured. In addition, the concentration of ions or other solutes present in body fluids can be detected and measured using this embodiment of the invention.

According to at least one embodiment, the connection port and/or the housing is attached to the collection tube or is formed integrally with the collection tube. Preferably, the assembly of collection tube, connection port and housing is a one-part member, for example made of plastic material. Alternatively, it is possible that the connection port and/or the housing is/are removably attached to the collection tube, for example to have the possibility to connect different types of connection ports and/or housings to the collection tube.

In at least one embodiment, the measuring device comprises a filter element disposed between the sensor element and the communication passage. This filter element mainly prevents the housing from being flooded with the aspirate.

Generally speaking, the measuring device comprises at least one sensor element and/or at least one filter element. That means it is also possible to measure different types of values, in particular by using a variety of sensor elements positioned adjacent, side-by-side or the like. Optionally, also several filter elements can be used.

According to at least one embodiment, the housing comprises a first support for the sensor element. In a further embodiment, the housing comprises a second support for the filter element. Of course, it is possible that the housing comprises further supports for further sensor elements and/or filter elements as described above. The supports can provide one or more supporting planes, which also means that the supports, sensor elements and/or filter elements can be placed adjacent or spaced apart from each other. Preferably, the first support and/or second support comprise at least one pin, plate, shim and/or edge.

According to at least one embodiment, the first support and/or the second support is/are configured and positioned relative to each other such that the sensor element is being spaced apart from the filter element.

In at least one embodiment, the housing comprises a lid, preferably with a transparent window. Further, it is possible that the entire lid and/or the entire housing is made of transparent material. The lid can be attached to the housing in removable manner. This provides the possibility to exchange the sensor element and/or the filter element within the housing.

According to at least one embodiment, the sensor element and/or the filter element comprises at least one absorbable material, which is preferably a sheet material, for example paper material and the like. The absorbable material is suitable for absorbing at least part of the aspirate drawn/entering into the housing.

To provide a fluid communication with the medical tube, the connection port preferably is configured to be connected to the medical tube or to a connector. Preferably, the connection port has a tapered and/or stepped end portion. Basically, it is possible that the collection tube comprises a piston or a syringe unit or is configured to be connected to a syringe to draw up the aspirate via a vacuum in the collection tube.

In at least one embodiment, the communication passage, which enables the aspirate to enter the housing, comprises a valve, preferably a spigot valve. Alternatively or additionally, the communication passage can be formed and/or can have dimensions such that the fluid aspirate is drawn from the collection tube into the housing.

Preferably, the physiological parameter is a pH value of the aspirate. In this case, preferably a pH indicator in the form of a pH indicative paper material is used for the sensor element.

According to at least one embodiment, the measuring device, in particular the housing, comprises an evaluation unit to evaluate the measured value. Preferably, a reference unit is attached to the lid of the housing, for example, a pH colour reference chart, which can be evaluated visually.

In at least one embodiment, the measuring device for measuring a physiological parameter of an aspirate comprises a sensor element for measuring the physiological parameter, a connection port for fluid communication with a medical tube, a collection tube for aspirating and/or collecting the aspirate, a housing with the sensor element is mounted within the housing, a communication passage enabling the aspirate to enter the housing from the collection tube such that the sensor element can measure the physiological parameter, a filter element disposed between the sensor element and the communication passage, wherein the housing comprises a first support for supporting the sensor element, a second support for supporting the filter element and a lid having a transparent window.

In at least one embodiment, as the physiological parameter the pH value is measured and a pH indicator paper is used for the sensor element. The closed system of the measuring device connects between the enteral access or giving device and a syringe which will aspirate or collect the aspirate of the stomach contents for both visual evaluation and pH measurement. A small amount of the aspirated fluid can be drawn in using a syringe vacuum via a spigot valve to the pH paper located behind the viewing window of the lid. A piece of absorbent paper as the filter element is also placed between the fluid entrance from the spigot valve and the pH paper, in order to prevent the viewing window from flooding with gastric residue or fluid, so that the colour change on the pH can be easily seen by the user. A pH colour reference chart can be supplied with the device. Preferably, this system or device is a single use, disposable device.

According to a further aspect, at least one embodiment relates to a method for measuring a physiological parameter of an aspirate. The method comprises the steps of connecting a connection port of the measuring device to a medical tube for fluid communication of the aspirate with a physiological parameter sensor element mounted in a housing of the measuring device, aspirating the aspirate out of the medical tube via a collection tube and a communication passage of the measuring device into the housing and measuring of the physiological parameter by means of the sensor element.

Preferably, in the step of aspirating (or drawing) the aspirate into the housing a vacuum is applied, e.g. by a syringe, and/or a valve is used. In order to measure the parameter, e.g. the pH value, an absorbable material can be used for the sensor element for absorbing part of the aspirate.

One advantage of the disclosed embodiment is that it provides a closed system having only few components, which is cost saving and does not create a mess that has to be cleaned up, as well as reducing the time taken to obtain the measured value, e.g. the pH value. The aspirated fluid drawn up travels in the closed system into and through the fluid communication passage into the housing containing and supporting the sensor element, e.g. the pH paper, to give a reading. Thus, it is not necessary to transport the amount of aspirate to be measured via a syringe to a different place and consequently there is no danger for nurses or clinicians to get into contact with a drop of the aspirate containing bacteria. The measuring device of this embodiment provides a dry solution to measure an aspirate's value and achieves easy determination of the medical tube's position.

A further advantage is that the measuring system of the disclosed embodiment can be used outside the patient's body simply by connecting the medical tube's end directly or indirectly to the measuring device.

What is claimed is:

1. A device for measuring a value of a physiological parameter of an aspirate, the device comprising:
    a housing;
    a sensor element for measuring the value of the physiological parameter, wherein the sensor element is mounted within the housing;
    a connection port for fluid communication with a medical tube;
    a collection tube for aspirating and/or collecting the aspirate;
    a communication passage enabling the aspirate to enter the housing from the collection tube such that the sensor element can measure the physiological parameter; and
    a filter element having an opening and disposed between the sensor element and the communication passage,
    wherein the housing comprises a first support for supporting the sensor element and a second support for supporting the filter element, the first support comprising at least one pin extending through the opening in the filter element, engaging an inner surface of the sensor element and spacing the sensor element from the filter element.

2. A device according to claim 1, further comprising a pH color reference chart attached to the housing, the chart providing for visual evaluation of the physiological parameter values.

* * * * *